(12) United States Patent
Davies et al.

(10) Patent No.: US 6,613,906 B1
(45) Date of Patent: Sep. 2, 2003

(54) CRYSTAL MODIFICATION

(75) Inventors: Julian Anthony Davies, Sylvania, OH (US); James E. Gano, Sylvania, OH (US)

(73) Assignee: Geneva Pharmaceuticals, Inc., Broomfield, CO (US)

( * ) Notice: Subject to any disclaimer, the term of this patent is extended or adjusted under 35 U.S.C. 154(b) by 0 days.

(21) Appl. No.: 09/588,391

(22) Filed: Jun. 6, 2000

(51) Int. Cl.$^7$ .............................................. C07D 211/34
(52) U.S. Cl. ........................................ 546/239; 546/239
(58) Field of Search .......................................... 546/239

(56) References Cited

U.S. PATENT DOCUMENTS

| | | | | |
|---|---|---|---|---|
| 4,254,129 A | * | 3/1981 | Carr et al. .................. | 546/239 |
| 5,574,045 A | | 11/1996 | Ortyl et al. ................. | 514/317 |
| 5,578,610 A | | 11/1996 | D'Ambra .................... | 514/317 |
| 5,618,940 A | | 4/1997 | King et al. ................. | 546/240 |
| 5,932,247 A | | 8/1999 | Ortyl et al. ................. | 424/252 |

FOREIGN PATENT DOCUMENTS

| | | | | |
|---|---|---|---|---|
| WO | WO 95/00480 | 1/1995 | ................. | 546/239 |
| WO | WO 95/31437 | 4/1995 | ................. | 546/239 |
| WO | WO 99/47693 | 9/1999 | ................. | 546/239 |
| WO | WO 00/21510 | 4/2000 | ................. | 546/239 |
| WO | WO 00/71124 | 11/2000 | ................. | 546/239 |

* cited by examiner

*Primary Examiner*—Alan L. Rotman
*Assistant Examiner*—Raymond Covington
(74) *Attorney, Agent, or Firm*—Gabriel Lopez; George R. Dohmann

(57) ABSTRACT

A novel crystal form of ,α-dimethyl-4-{1-hydroxy-4-{4-(hydroxydiphenylmethyl)-1-piperidinyl}butyl}benzeneacetic acid hydrochloride, processes for its preparation and its pharmaceutical use are disclosed.

22 Claims, 4 Drawing Sheets

CRYSTAL MODIFICATION

SUMMARY

This invention relates to a novel crystal form of α,α-dimethyl-4-{1-hydroxy4-{4-(hydroxydiphenylmethyl)-1-piperidinyl}butyl}benzeneacetic acid hydrochloride, a process for its preparation and pharmaceutical formulations thereof.

BACKGROUND

The compound α,α-dimethyl-4-{1-hydroxy-4-{4-(hydroxydiphenylmethyl)-1-piperidinyl}butyl}benzeneacetic acid hydrochloride has been named according to the U.S.A.N. as fexofenadine hydrochloride ("F-HCl"). It is known as the active metabolite of the non-sedating antihistamine terfinadine and is itself marketed in the United States as a non-sedating antihistamine. F-HCl and its preparation are described, for example, in U.S Pat. No. 5,578,610, which is here incorporated by reference. Anhydrous and hydrated crystal forms of F-HCl identified as Forms I, II, III and IV are described in WO 95/31437.

The present invention relates to a novel F-HCl crystal modification, hereinafter designated as Form A, which is distinguished from previously known crystal forms by physical and spectroscopic properties such as melting point, x-ray powder diffraction pattern, solid state NMR spectrum and infrared spectrum. The Form A crystal modification of F-HCl is prepared in an advantageously environmentally friendly manner.

DETAILED DESCRIPTION

The Form A crystal modification of F-HCl is characterized by its physical and spectroscopic properties which are described in detail below.

The Form A crystal modification of F-HCl has a characteristic melting point in the range from about 138° C. to 148° C., more specifically about 142° C. to about 145° C.

Figure 1:
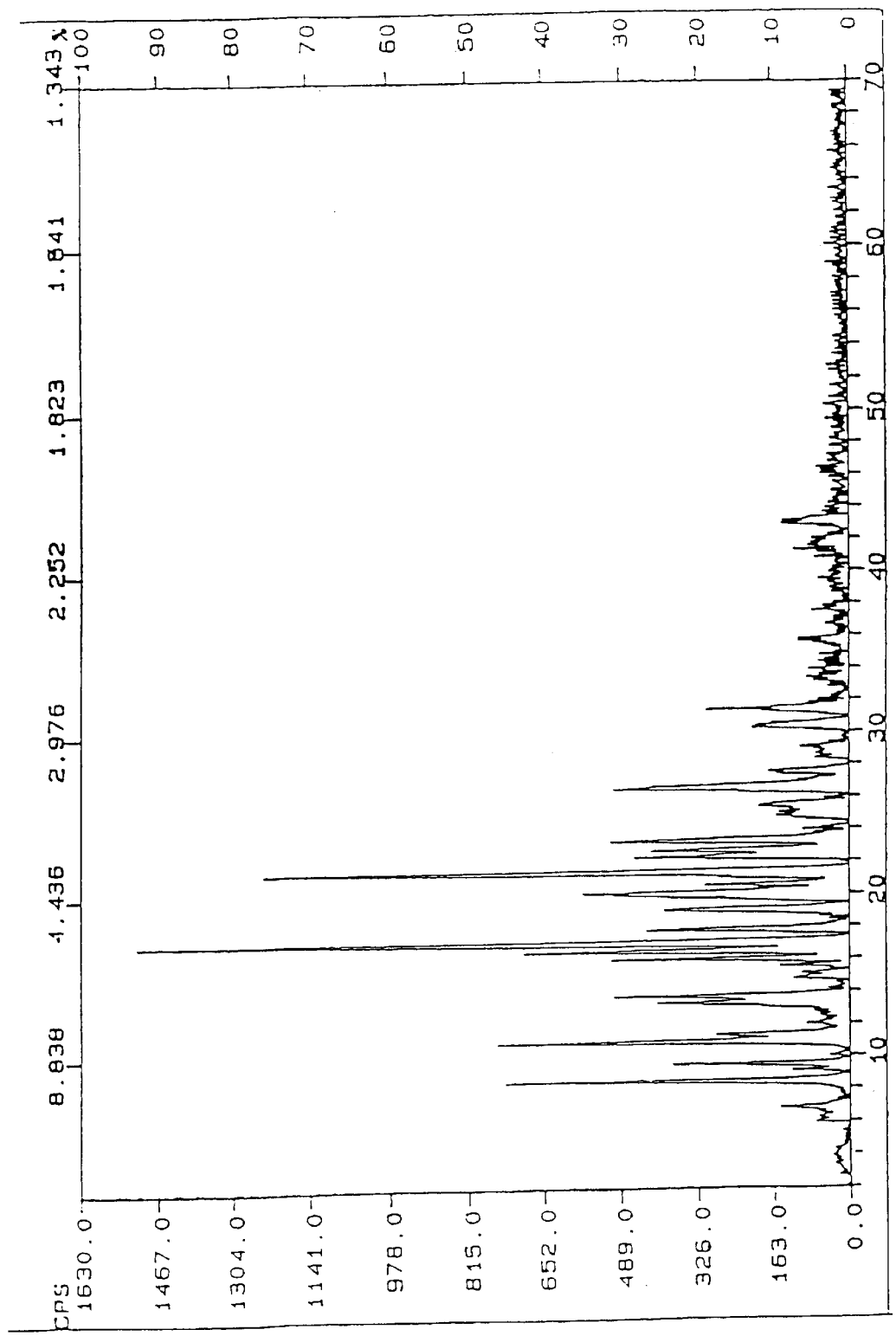
FIG. 1 shows the powder x-ray diffraction pattern of the Form A crystal modification of F-HCl (λ=1.540600).

FIG. 1 is the powder x-ray diffraction pattern of the Form A crystal modification of F-HCl. The powder x-ray diffraction pattern of Form A is characterized by peaks at about 10.5, 8.1, 5.5, 5.4, 5.2, 4.42, 4.15, 3.82, 3.35 d-spacing units. The x-ray diffraction pattern depicted in FIG. 1 is summarized in Table 1:

TABLE 1

Powder X-Ray Diffraction Peaks for the Form A crystal modification of F—HCl

| Peak No. | °2θ[1] | d-space[1] | RELATIVE INTENSITY[2] |
|---|---|---|---|
| 1 | 5.99 | 14.74 | 4 |
| 2 | 6.59 | 13.40 | 4 |
| 3 | 6.83 | 12.91 | 9 |

TABLE 1-continued

Powder X-Ray Diffraction Peaks for the Form A crystal modification of F—HCl

| Peak No. | °2θ[1] | d-space[1] | RELATIVE INTENSITY[2] |
|---|---|---|---|
| 4 | 8.42 | 10.49 | 45 |
| 5 | 9.09 | 9.71 | 7 |
| 6 | 9.47 | 9.32 | 23 |
| 7 | 10.85 | 8.14 | 48 |
| 8 | 11.29 | 7.83 | 18 |
| 9 | 11.97 | 7.39 | 5 |
| 10 | 12.45 | 7.09 | 4 |
| 11 | 13.26 | 6.66 | 26 |
| 12 | 13.67 | 6.46 | 31 |
| 13 | 14.80 | 5.93 | 7 |
| 14 | 15.08 | 5.86 | 6 |
| 15 | 15.54 | 5.69 | 9 |
| 16 | 15.97 | 5.54 | 31 |
| 17 | 16.46 | 5.37 | 44 |
| 18 | 17.02 | 5.29 | 100 |
| 19 | 17.80 | 4.97 | 27 |
| 20 | 19.01 | 4.65 | 26 |
| 21 | 20.05 | 4.42 | 36 |
| 22 | 20.57 | 4.31 | 19 |
| 23 | 21.38 | 4.15 | 82 |
| 24 | 22.27 | 3.98 | 28 |
| 25 | 22.68 | 3.91 | 27 |
| 26 | 23.29 | 3.81 | 33 |
| 27 | 24.82 | 3.53 | 9 |
| 28 | 25.03 | 3.55 | 9 |
| 29 | 25.45 | 3.49 | 12 |
| 30 | 26.55 | 3.35 | 33 |
| 31 | 27.50 | 3.24 | 11 |
| 32 | 29.09 | 3.06 | 6 |
| 33 | 30.31 | 2.94 | 13 |
| 34 | 31.40 | 2.34 | 17 |
| 35 | 31.82 | 2.81 | 5 |
| 36 | 33.34 | 2.68 | 5 |
| 37 | 35.66 | 2.51 | 5 |
| 38 | 35.78 | 2.50 | 5 |
| 39 | 41.29 | 2.13 | 6 |
| 40 | 41.55 | 2.17 | 5 |
| 41 | 41.73 | 2.16 | 5 |
| 42 | 42.90 | 2.13 | 9 |
| 43 | 43.09 | 2.09 | 9 |

[1]- peak values reported in Table 1 are truncated to 2 decimal places from the instrument report and reported without regard to significant figures
[2]- intensities may vary significantly due to orientation effects Variances in the d-spacing values reported for any x-ray diffraction peak within ±1% are considered insignificant. The use of the expression "about" when describing the position of an powder-ray diffraction peak is intended to provide a basis for including such insignificant variances within the characterization of the Form A crystal modification.

Figure 2:
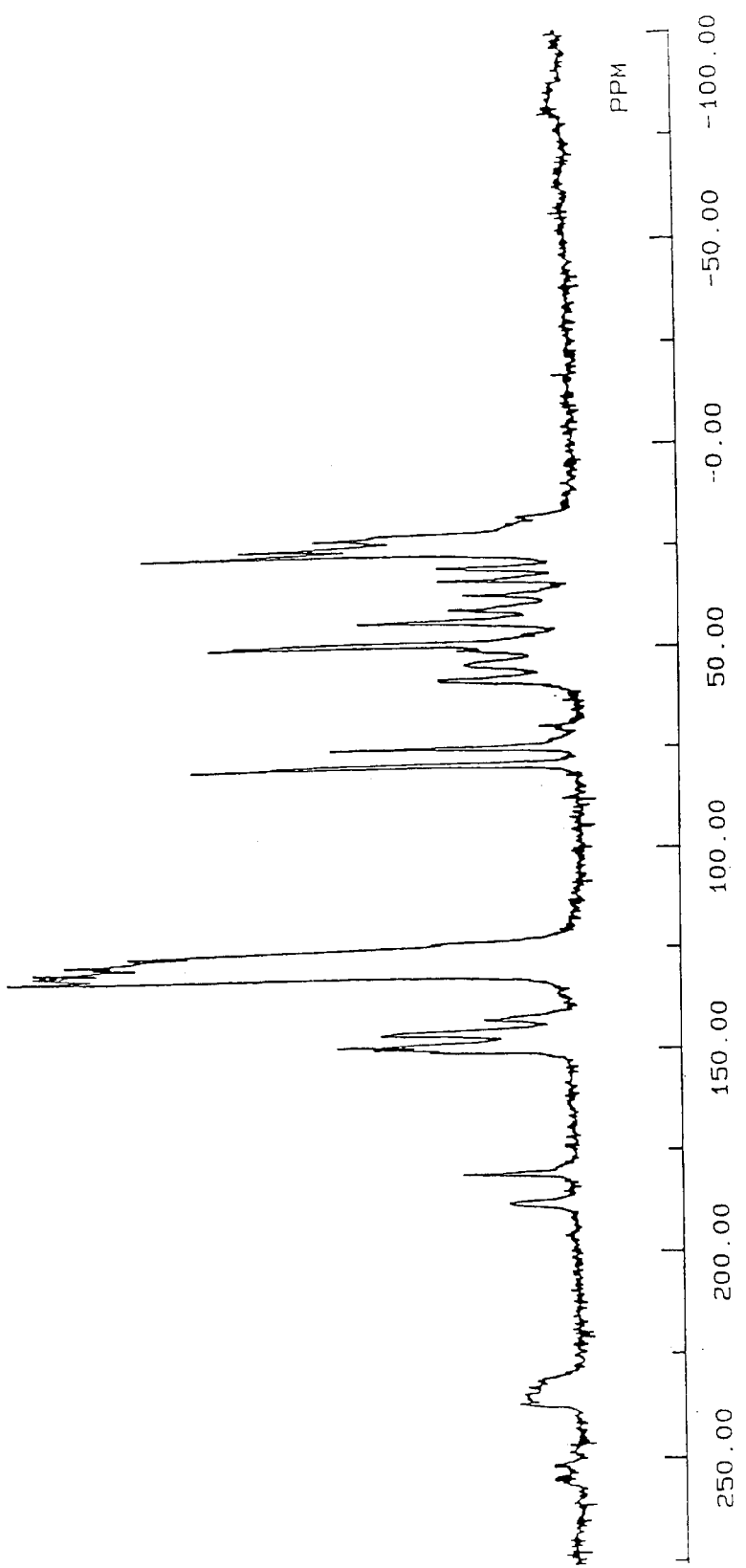
FIG. 2 shows the solid state Carbon-13 NMR of the Form A crystal modification of F-HCl over the chemical shift range of 275 to −100 ppm.

FIG. 2 shows the carbon-13 NMR spectrum of the Form A crystal modification of F-HCl measured using 600 transients and a 6 second pulse delay over the chemical shift range of 275 to −100 ppm. Characteristic signals are observed: at chemical shifts of 187.4, 180.3, 74.5, 48.8 and 29.8 ppm. Table 2 summarizes the signals observed in the solid state carbon-13 NMR of the Form A crystal modification of F-HCl.

TABLE 2

Solid State NMR Signals of The Form A crystal modification of F-HCl

| peak # | p.p.m. |
|---|---|
| 1 | 187.4 |
| 2 | 180.3 |
| 3 | 148.3 |
| 4 | 145.6 |
| 5 | 142.0 |
| 6 | 130.4* |
| 7 | 128.2* |
| 8 | 126.4* |
| 9 | 78.9* |
| 10 | 74.5 |
| 11 | 57.5 |
| 12 | 53.9 |
| 13 | 48.8* |
| 14 | 43.2 |
| 15 | 40.2 |
| 16 | 36.5 |
| 17 | 32.9 |
| 18 | 29.8 |
| 19 | 26.0* |
| 20 | 24.6* |
| 21 | 22.6 |

*denotes most intense signals

The chemical shifts reported for solid state carbon-13 NMR signals can vary from sample to sample by up to 1 ppm. The use of the expression "about" to describe the chemical shift of an NMR signal is intended to include such variances within the characterization of the Form A crystal modification.

One or more of physical properties and/or spectroscopic properties are the basis for characterizing the Form A crystal modification of F-HCI.

For example, the Form A crystal modification of F-HCI is properly described as α,α-dimethyl-4-{1-hydroxy-4-{4-(hydroxydiphenylmethyl)-1-piperidinyl}butyl}benzeneacetic acid hydrochloride having a melting point in the range from 138° C. to 148° C., or as α,α-dimethyl-4-{1-hydroxy-4-{4-(hydroxydiphenylmethyl)-1-piperidinyl}butyl}benzeneacetic acid hydrochloride having a melting point in the range from about 142° C. to about 145° C. It is also properly described as crystalline α,α-dimethyl4-{1-hydroxy-4-{4-(hydroxydiphenylmethyl)-1-piperidinyl}butyl}benzeneacetic acid hydrochloride having powder x-ray diffraction peaks at d spacings of 10.5, 8.1, 5.5, 5.4, 5.2, 4.42, 4.15, 3.82, 3.35 or the x-ray diffraction pattern depicted in Table 1. It is also properly described as α,α-dimethyl-4-{1-hydroxy-4-{4-(hydroxydiphenylmethyl)-1-piperidinyl}butyl}benzeneacetic acid hydrochloride having solid state carbon-13 NMR signals at chemical shifts of 187.4, 180.3, 74.5, 48.8, and 29.8 ppm, or as having the solid state carbon-13 NMR spectrum depicted in FIG. 2 and Table 2. It is also properly described as α,α-dimethyl-4-{1-hydroxy-4-{4-(hydroxydiphenylmethyl)-1-piperidinyl}butyl}benzeneacetic acid hydrochloride having the Fourier Transform Infrared Spectrum depicted in FIG. 3A as a Nujol oil mull.

The Form A crystal modification is also properly described by a combination of physical and/or spectroscopic properties.

Thus, Form A F-HCI is a substantially pure crystal modification of α,α-dimethyl-4-{1-hydroxy-4-{4-(hydroxydiphenylmethyl)-1-piperidinyl}butyl}benzeneacetic acid hydrochloride characterized by powder x-ray diffraction peaks at d spacings of about 10.5, 8.1, 5.5, 5.4, 5.2, 4.42, 4.15, 3.82, 3.35 and a melting point in the range from about 142° C. to about 145° C.

Form A F-HCI is also a crystal modification of α,α-dimethyl-1-{1-hydroxy-4-{4-(hydroxydiphenylmethyl)-1-piperidinyl}butyl)benzeneacetic acid hydrochloride characterized by solid state carbon-13 NMR signals at chemical shifts of about 187.4, 180.3, 74.5, 48.8, and 29.8 ppm and powder x-ray diffraction peaks at d spacings of about 10.5, 8.1, 5.5, 5.4, 5.2, 4.42, 4.15, 3.82, 3.35. It is also such a crystal modification having a melting point in the range from about 142° C. to about 145° C. in pure form.

Form A F-HCI is also properly described as a crystal modification having the solid state carbon-13 NMR spectrum depicted in FIG. 2 and the x-ray powder diffraction pattern depicted in FIG. 1. It is also such a crystal modification having the Fourier Transform Infrared Spectrum depicted in FIG. 3A as a Nujol oil mull and can be further characterized as having a melting point in the range from 138° C. to 148° C. in substantially pure form, preferably from about 142° C. to about 145° C. in pure form.

Preferably, the Form A crystal modification of F-HCI is in substantially pure form—substantially pure form being intended to mean that at least 80 percent by weight of the crystalline F-HCI in the sample is present as Form A. Most preferably, the Form A crystal modification is in pure form meaning that at least 90% of the crystalline F-HCI in the sample is present as Form A. The present invention also relates :to highly pure Form A crystal modification meaning that the material is essentially homogeneous Form A crystal modification.

The Form A crystal modification of F-HCI is prepared in an environmentally friendly manner by crystallization from an aqueous solution of F-HCI at a temperature in the range from 5° C. to 50° C., preferably in the range from 20° C. to 40° C. Generally, a temperature of about 30° C. is optimal. If the crystallization is carried out at the higher and lower temperatures in the above defined temperature ranges the resulting product can be a mixture of crystal forms which includes Form A.

Generally, crystalline or non-crystalline F-HCI is dissolved in water with stirring to form an aqueous solution of F-HCI. The temperature of the aqueous solution of F-HCI is then adjusted to the desired temperature range, for example, by placing it in a water or oil bath, the solution is stirred and the water allowed to partially evaporate to yield Form A crystals of F-HCI. Preferably, the evaporation of the water is assisted, for example, by passing a gentle stream of air over the surface of the solution or reducing the pressure above the solution. However, the solution should be maintained in the temperature ranges identified above while the water evaporates from the solution.

Advantageously, no co-solvent or additional organic material is present in the water used to prepare the aqueous solution. However, minor amounts of such co-solvents or additional organic materials are not known to cause any significant disadvantage.

Thus, the present invention relates to a method of preparing the Form A crystal modification of α,α-dimethyl-4-{1-hydroxy-4-{4-(hydroxydiphenylmethyl)-1-piperidinyl}butyl}benzeneacetic acid hydrochloride, which comprises preparing an aqueous solution of α,α-dimethyl-4-{1-hydroxy-4-{4-(hydroxydiphenylmethyl)-1-piperidinyl}butyl}benzeneacetic acid hydrochloride; and crystallizing the α,α-dimethyl-4-{1-hydroxy-4-{4-(hydroxydiphenylmethyl)-1-piperidinyl}butyl}benzeneacetic acid hydrochloride form the aqueous solution at a temperature of from 5° C. to 50° C. Preferably, the crystallization is carried out at a temperature of 20° C. to 40° C. Optimally, the crystallization is carried out at a temperature in the range from 25° C. to 35° C., most optimally at about 30° C.

The crystallization step is effected by methods known in the art for precipitating a solute from solution, for example, by reducing the volume of solvent by evaporation or other means, or by addition of a co-solvent which induces crystallization and seeding.

Preferably, the crystallization step is effected by reducing the volume of water in the aqueous solution. Thus, the present invention further relates to a process wherein the crystallization step is effected by reducing the volume of water in the aqueous solution by an amount sufficient to promote crystallization. Preferably, the volume of water is reduced by evaporation of the water. This can be assisted by blowing a stream of air over the surface of the aqueous solution or by reducing the pressure above the solution in some other way.

The Form A crystal modification of F-HCl is used, in particular, for the preparation of pharmaceutical compositions of F-HCl. Thus, the present invention further relates to a pharmaceutical composition which comprises a pharmaceutically effective amount of the Form A crystal modification of α,α-dimethyl-4-{1-hydroxy-4-{4-(hydroxydiphenylmethyl)-1-piperidinyl}butyl}benzeneacetic acid hydrochloride. Preferably, the pharmaceutically effective amount is the amount required to deliver 50 to 150 mg/day.

The following example is intended to illustrate, but not limit, the invention. All melting points are uncorrected unless otherwise noted.

EXAMPLE 1

A 0.51 gram sample of F-HCl (melting point range from 192° C. to 198° C.) is dissolved in 100 mL of deionized water by heating on a water bath at 80° C. and stirring at moderate speed with a 1 cm Teflon coated magnetic stirring bar. The temperature of the aqueous solution is reduced to 30° C. and held at that temperature in the water bath as a gentle stream of air is passed over the surface. After about half of the water evaporates (approximately 7 hours), the crystalline precipitate of Form A F-HCl is separated by vacuum filtration with a Hirsch funnel. The sample is protected from dust by a filter paper cover and allowed to dry in the air for approximately 48 hours.

Figure 3:
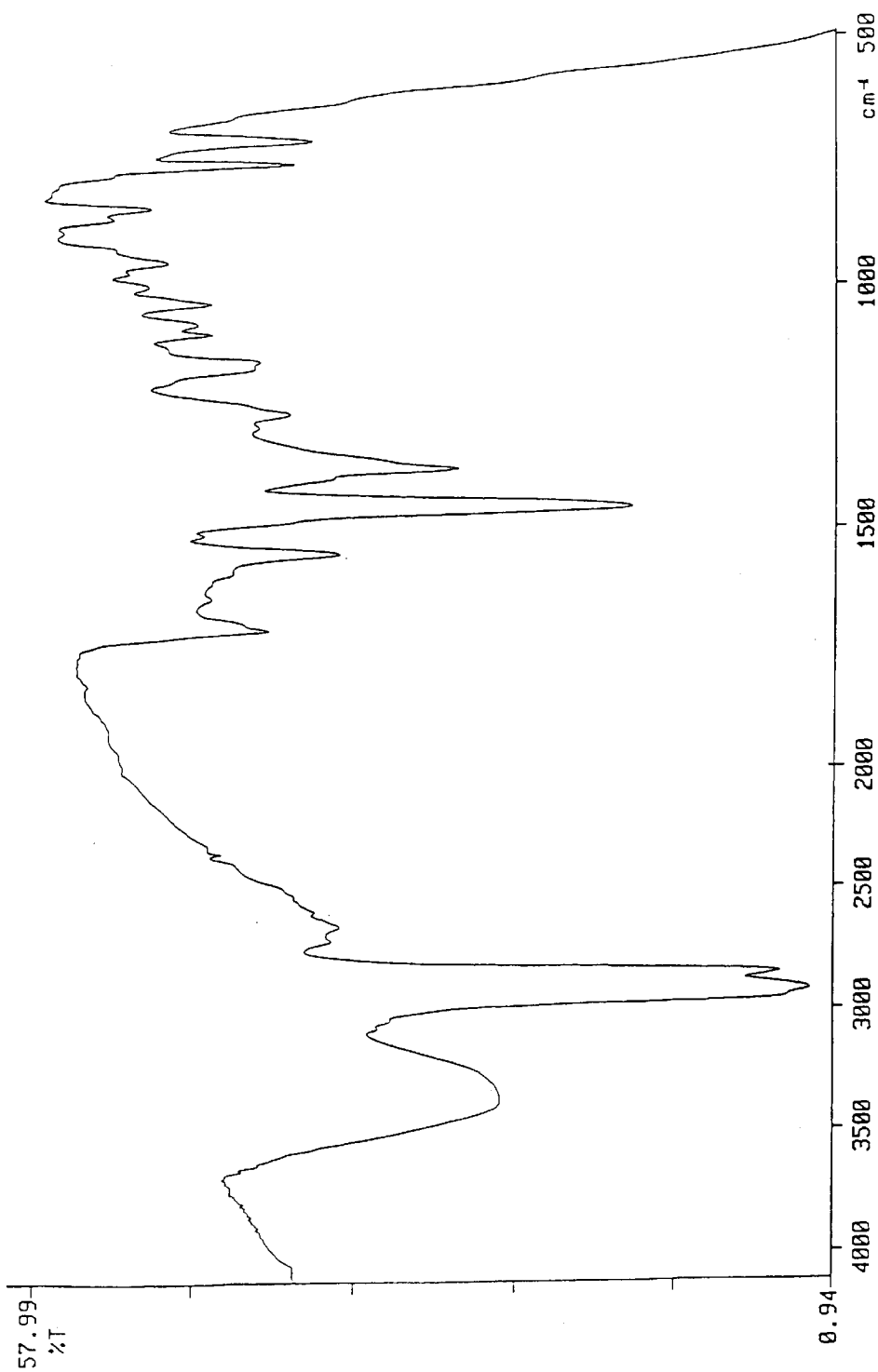
FIG. 3 shows the FTIR spectrum of the Form A crystal modification of F-HCl as a mull with Nujol oil.
Figure 4:
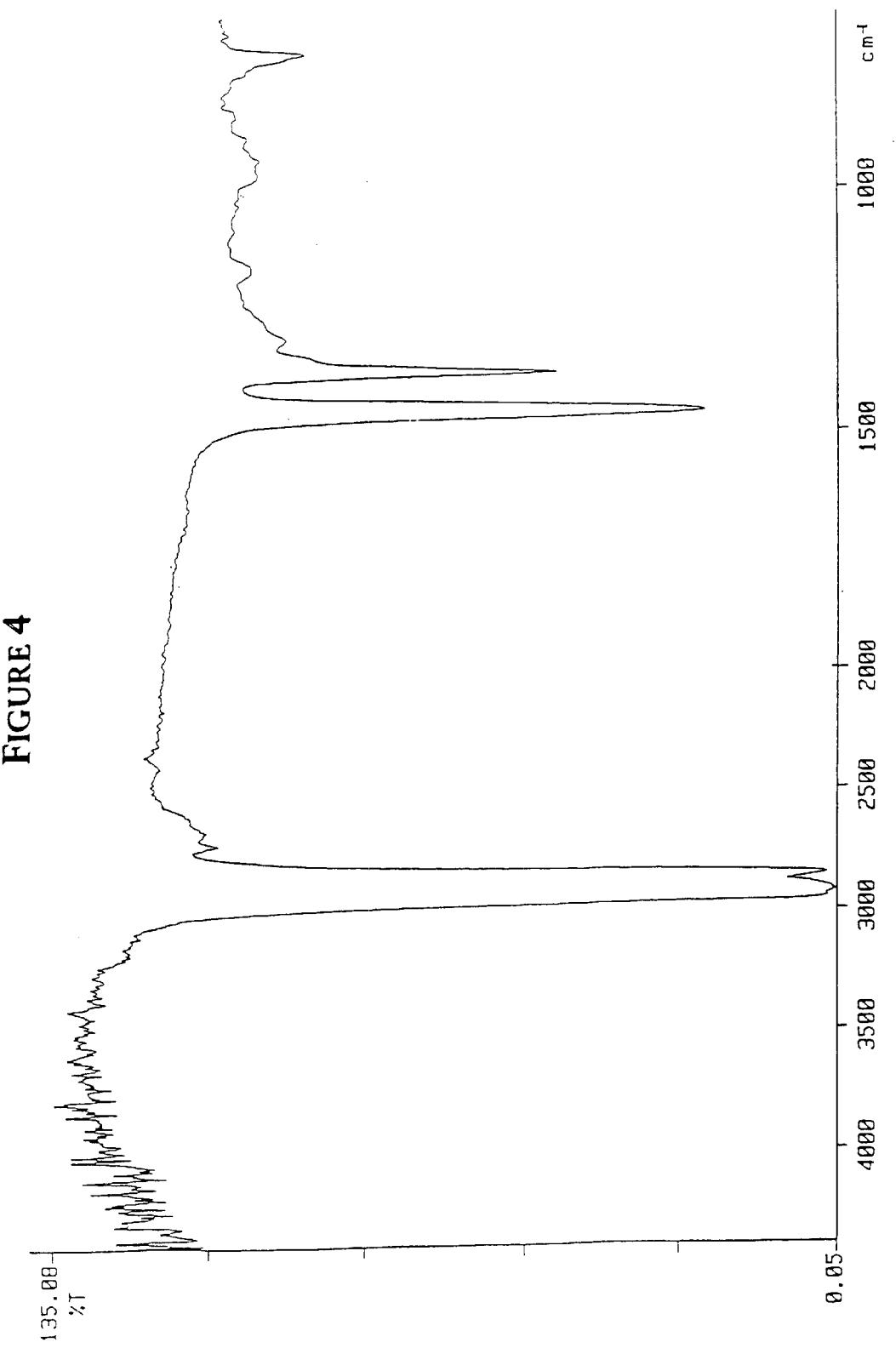
FIG. 4 shows the FTIR spectrum of Nujol oil.

The Form A F-HCl thus prepared exhibits a melting point of 142° C. to 145° C., determined in an open glass capillary suspended in circulating oil using a Thomas Hoover Melting Point Apparatus, the powder x-ray diffraction pattern is depicted in FIG. 1 and Table 1, the solid state carbon-13 NMR spectrum depicted in FIG. 2 and Table 2, and the FTIR spectrum depicted in FIG. 3 as a Nujol mull.

We claim:

1. The compound α,α-dimethyl-4-{1-hydroxy-4-{4-(hydroxydiphenylmethyl)-1-piperidinyl}butyl}benzeneacetic acid hydrochloride having a melting point in the range from 138° C. to 148° C.

2. The compound α,α-dimethyl-4-{1-hydroxy-4-(hydroxydiphenylmethyl)-1-piperidinyl}butyl}benzeneacetic acid hydrochloride having a melting point in the range from about 142° C. to about 145° C.

3. A crystal modification of α,α-dimethyl-4-{1-hydroxy-4-{4-(hydroxydiphenylmethyl)-1-piperidinyl}butyl}benzeneacetic acid hydrochloride characterized by powder x-ray diffraction peaks at d spacings of about 10.5, 8.1, 5.5, 5.4, 5.2, 4,.42, 4.15, 3.82, 3.35.

4. The crystal modification of claim 3 having the powder x-ray diffraction pattern depicted in FIG. 1.

5. The crystal modification of claim 3 characterized by, a melting point in the range from about 142° C. to about 145° C.

6. A crystal modification of α,α-dimethyl-4-{1-hydroxy-4-{4-(hydroxydiphenylmethyl)-1-piperidinyl}butyl}benzeneacetic acid hydrochloride characterized by solid state carbon-13 NMR signals at chemical shifts of about 187.4, 180.3, 74.5, 48.8, and 29.8 ppm.

7. The crystal modification of claim 6 having the solid state carbon-13 NMR spectrum depicted in FIG. 2.

8. The crystal modification of claim 6 having powder Gray diffraction peaks at d spacings of about 10.5, 8.1, 5.5, 5.4, 5.2, 4.42, 4.15, 3.82, 3.35.

9. The crystal modification of claim 8 having a melting point in the range from about 142° C. to about 145° C.

10. The crystal modification of claim 8 having a melting point in the range from about 138° C. to 148° C.

11. The crystal modification of claim 7 having the powder x-ray diffraction pattern depicted in FIG. 1.

12. The crystal modification of claim 11 having the Fourier Transform Infrared Spectrum depicted in FIG. 3 as a Nujol oil mull.

13. The crystal modification of claim 12 having a melting point in the range from about 138° C. to about 148° C. in substantially pure form.

14. The crystal modification of claim 13 having a melting point in the range from about 142° C. to about 145° C. in pure form.

15. The crystal modification of claim 14 in highly pure form.

16. A process for preparing the compound of claim 1, which comprises (a) preparing an aqueous solution of α,α-dimethyl-4-{1-hydroxy-4-{4-(hydroxydiphenylmethyl)-1-piperidinyl}butyl}benzeneacetic acid hydrochloride; and (b) crystallizing the α,α-dimethyl-4-{1-hydroxy-4-{4-(hydroxydiphenylmethyl)-1-piperidinyl}butyl}-benzeneacetic acid hydrochloride from the aqueous solution at a temperature of from 5° C. to 50° C.

17. A process of claim 16 wherein the temperature is in the range from 20° C. to 40° C.

18. A process of claim 17 wherein the temperature is in the range from 25° C. to 35° C.

19. A process of claim 18 wherein the temperature is about 30° C.

20. A process of claim 16 wherein the crystallization step is effected by reducing the volume of water in the aqueous solution by an amount sufficient to promote crystallization.

21. A process of claim 19 wherein the crystallization step is effected by reducing the volume of water in the aqueous solution by an amount sufficient to promote crystallization.

22. A process of claim 21 wherein the volume of water is reduced by evaporation.

* * * * *

UNITED STATES PATENT AND TRADEMARK OFFICE
CERTIFICATE OF CORRECTION

PATENT NO.    : 6,613,906 B1
DATED         : September 2, 2003
INVENTOR(S)   : Davies et al.

It is certified that error appears in the above-identified patent and that said Letters Patent is hereby corrected as shown below:

Title page,
Item [*] Notice, should read -- Subject to any disclaimer, the term of this patent is extended or adjusted under 35 U.S.C. 154(b) by 36 days. --

Column 1,
Line 6, should read -- dimethyl-4-}1-hydroxy-4-}4-(hydroxydiphenylmethyl)-1- --.

Column 3,
Line 46, should read -- dimethyl-4-}1-hydroxy-4-}4-(hydroxydiphenylmethyl)-1- --.

Column 4,
Line 7, should read -- dimethyl-4-}1-hydroxy-4-}4-(hydroxydiphenylmethyl)-1- --.

Column 5,
Line 3, should read -- piperidinyl}butyl}benzeneacetic acid hydrochloride from --.
Line 64, should read -- }4-(hydroxydiphenylmethyl)-1- --.

Column 6,
Line 20, should read -- x-ray diffraction peaks at d spacings of about 10.5, 8.1, 5.5, --.

Signed and Sealed this

Twelfth Day of October, 2004

JON W. DUDAS
*Director of the United States Patent and Trademark Office*